US006746854B2

(12) United States Patent
Bathe et al.

(10) Patent No.: US 6,746,854 B2
(45) Date of Patent: Jun. 8, 2004

(54) NUCLEOTIDE SEQUENCES ENCODING HISTIDINE KINASE FROM CORYNEBACTERIUM GLUTAMICUM

(75) Inventors: Brigitte Bathe, Salzkotten (DE); Caroline Kreutzer, Melle (DE); Achim Marx, Bielefeld (DE); Walter Pfefferle, Halle (DE)

(73) Assignee: Degussa AG, Düsseldorf (DE)

( * ) Notice: Subject to any disclaimer, the term of this patent is extended or adjusted under 35 U.S.C. 154(b) by 0 days.

(21) Appl. No.: 09/824,551

(22) Filed: Aug. 1, 2001

(65) Prior Publication Data

US 2002/0182689 A1 Dec. 5, 2002

(30) Foreign Application Priority Data

Sep. 9, 2000 (DE) .......................... 100 44 755
Mar. 14, 2001 (DE) .......................... 101 12 105

(51) Int. Cl.⁷ .............................. C12P 13/08
(52) U.S. Cl. .................. 435/115; 536/23.2; 536/23.7; 435/320.1; 435/252.32; 435/252.33; 435/252.3
(58) Field of Search .............. 435/115, 320.1, 435/252.3, 252.32, 252.33; 536/23.2, 23.7, 23.1

(56) References Cited

U.S. PATENT DOCUMENTS

2002/0197605 A1 * 12/2002 Nakagawa et al.

FOREIGN PATENT DOCUMENTS

EP    0 435 132    7/1990
EP    1 108 790    6/2001

OTHER PUBLICATIONS

Birren et al. GenBank Accession No. AC018367. *Homo sapiens* clone RP11–46B20. Published Mar. 28, 2000.*

Kramer, et al., "Genetic and physiological approaches for the production of amino acids," Journal of Biotechnology, vol. 45, No. 1, 1996, p. 1–21.

Peters–Wendisch, et al., "Pyruvate carboxylase from Corynebacterium glutamicum: characterization, expression and inactivation of the pyc gene," Microbiology, vol. 144, No. 4, 1998, p. 915–927.

* cited by examiner

*Primary Examiner*—Rebecca E. Prouty
*Assistant Examiner*—Kathleen Kerr
(74) *Attorney, Agent, or Firm*—Pillsbury Winthrop LLP

(57) ABSTRACT

This invention relates to novel polynucleotide sequences encoding the histidine kinase luminescence expression sensor (luxS) gene from *Corynebaclerium glutamicum*, probes to the novel polynucleotide sequences encoding the luxS gene, vector and host cells containing the novel luxS polynucleotide sequences, the encoded Lux S polypeptide, and a process for the fermentative preparation of amino acids using bacteria which the luxS gene is attenuated.

7 Claims, 1 Drawing Sheet

Figure 1: Plasmid pCR2.1luxSint
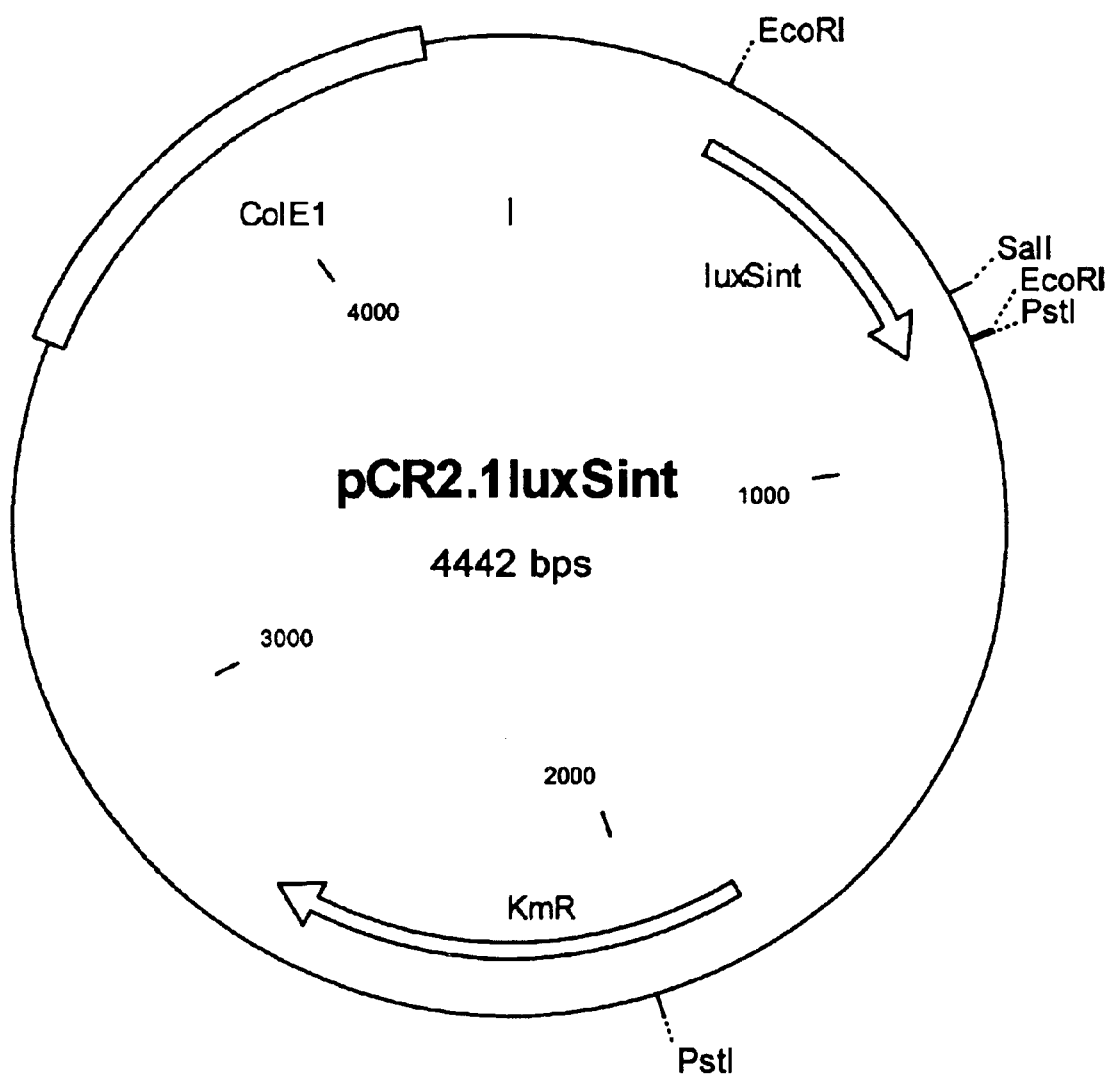

NUCLEOTIDE SEQUENCES ENCODING HISTIDINE KINASE FROM CORYNEBACTERIUM GLUTAMICUM

The invention provides nucleotide sequences from coryneform bacteria which cod for the histidine kinase luminescence expression sensor (luxS) gene and a process for the fermentative preparation of amino acids using bacteria in which the luxS gene is attenuated.

BACKGROUND OF THE INVENTION

L-Amino acids, in particular lysine, are used in human medicine and in the pharmaceuticals industry, in the foodstuffs industry and very particularly in animal nutrition.

It is known that amino that amino acids are prepared by fermentation from strains of coryneform bacteria, in particular *Corynebacterium glutamicum*. Because of their great importance, work is constantly being undertaken to improve the preparation processes. Improvements to the process can relate to fermentation measures, such as, for example, stirring and supply of oxygen, or the composition of the nutrient media, such as, for example, the sugar concentration during the fermentation, or the working up to the product form by, for example, ion exchange chromatography, or the intrinsic output properties of the microorganism itself.

Methods of mutagenesis, selection and mutant selection are used to improve the output properties of these microorganisms. Strains which are resistant to antimetabolites or are auxotrophic for metabolites of regulatory importance and which produce amino acids are obtained in this manner.

Methods of the recombinant DNA technique have also been employed for some years for improving the stain of Corynebacterium strains which produce L-amino acid, by amplifying individual amino acid biosynthesis genes and investigating the effect on the amino acid production.

OBJECT OF THE INVENTION

The inventors had the object of providing new measures for improved fermentative preparation of amino acids.

SUMMARY OF THE INVENTION

Where L-amino acids of amino acids are mentioned in the following, this means one or more amino acids, including their salts, chosen from the group consisting of L-glycine, asparagine, L-threonine, L-serine, L-glutamate, L-glycine, L-alanin, L-cysteine, L-valine, L-methionine, L-isoleucine, L-leucine, L-tyrosine, L-phenylalanine, L-histidine, L-lysine, L-tryptophan and L-arginine. Lysine is particularly preferred.

When L-lysine or lysine are mentioned in the following, not only the bases but also the salts, such as e.g. lysine monohydrochloride or lysine sulfate, are meant by this.

The invention provides an isolated polynucleotide from coryneform bacteria, comprising a polynucleotide sequence which codes for the luxS gene, chosen from the group consisting of a) polynucleotide which is identical to the extent of at least 70% to a polynucleotide which codes for a polypeptide which comprises the amino acid sequence of SEQ ID No. 2, b) polynucleotide which codes for a polypeptide which comprises an amino acid sequence which is identical to the extent of at least 70% to the amino acid sequence of SEQ ID No. 2, c) polynucleotide which is complementary to the polynucleotides of a) or b), and d) polynucleotide comprising at least 15 successive nucleotides of the polynucleotide sequence of a), b) or c), the polypeptide preferably having the activity of the histidine kinase LuxS.

The invention also provides the abovementioned polynucleotide, this preferably being a DNA which is capable of replication, comprising:

(i) the nucleotide sequence, shown in SEQ ID No.1, or (ii) at least one sequence which corresponds to sequence (i) within the range of the degeneration of the genetic code, or (iii) at least one sequence which hybridizes with the sequences complementary to sequences (i) or (ii), and optionally (iv) sense mutations of neutral function in (i).

The invention also provides:

a polynucleotide, in particular DNA, which is capable of replication and comprises the nucleotide sequence as shown in SEQ ID No.1;

a polynucleotide which codes for a polypeptide which comprises the amino acid sequence as shown in SEQ ID No.2;

a vector containing parts of the polynucleotide according to the invention, but at least 15 successive nucleotides of the sequence claimed, and coryneform bacteria in which the luxS gene is attenuated, in particular by an insertion or deletion.

The invention also provides polynucleotides which substantially comprise a polynucleotide sequence, which are obtainable by screening by means of hybridization of a corresponding gene library of a coryneform bacterium, which comprises the complete gene or parts thereof, with a probe which comprises the sequence of the polynucleotide according to the invention according to SEQ ID No.1 or a fragment thereof, and isolation of the polynucleotide sequence mentioned.

Polynucleotides which comprises the sequence according to the invention are suitable as hybridization probes for RNA, cDNA and DNA, in order to isolate, in the full length, nucleic acids or polynucleotides or genes which code for the histidine kinase LuxS or to isolate those nucleic acids or polynucleotides or genes which have a high similarity with the sequence the luxS gene.

Polynucleotides which comprises the sequences according to the invention are furthermore suitable are primers with the aid of which DNA of genes which code for the histidine kinase LuxS can be prepared by the polymerase chain reaction (PCR).

Such oligonucleotides which serve as probes or primers comprise at least 30, preferably at least 20, very particularly preferably at least 15 successive nucleotides. Oligonucleotides which have a length of at least 40 or 50 nucleotides are also suitable.

DETAILED DESCRIPTION OF THE INVENTION

FIG. 1: Map of the plasmid pCR2.1 luxSint.

The abbreviations and designations used have the following meaning.

KmR: Kanamycin resistance gene

EcoRI: Cleavage site of the restriction enzyme EcoRI

PstI: Cleavage site of the restriction enzyme PstI

SalI: Cleavage site of the restriction enzyme SalI luxSint: Internal fragment of the luxS gene ColE1: Replication origin of the plasmid ColE1.

"Isolated" means separated out of its natural environment.

BRIEF DESCRIPTION OF THE DRAWINGS

FIG. 1 shows the shuttle and integration plasmid pCR2.luxSint containing the 492 bp internal fragment of the luxS gene.

DETAILED DESCRIPTION OF THE INVENTION

"Polynucleotide" in general relates to polyribonucleotides and polydeoxyribonucleotides, it being possible for these to be non-modified RNA or DNA or modified RNA or DNA.

The polynucleotides according to the invention include a polynucleotide according to SEQ ID No. 1 or a fragment prepared therefrom and also those which are at least 70%, preferably at least 80% and in particular at least 90% to 95% identical to the polynucleotide according to SEQ ID No. 1 or a fragment prepared therefrom.

"Polypeptides" are understood as meaning peptides or proteins which comprise two or more amino acids bonded via peptide bonds.

The polypeptides according to the invention include a polypeptide according to SEQ ID No. 2, in particular those with the biological activity of the histidine kinase LuxS, and also those which are at least 70%, preferably at least 80% and in particular at least 90% to 95% identical to the polypeptide according to SEQ ID No. 2 and have the activity mentioned.

The invention furthermore relates to a process for the fermentative preparation of amino acid chosen from the group consisting of L-asparagine, L-threonine, L-serine, L-glutamate, L-glycine, L-alanine, L-cysteine, L-valine, L-methionine, L-isoleucine, L-leucine, L-tyrosine, L-phenylalanine, L-histidine, L-lysine, L-tryptophan and L-arginine using coryneform bacteria which in particular already produce amino acids and in which the nucleotide sequences which code for the luxS gene are attenuated, in particular eliminated or expressed at a low level.

The term "attenuation" in this connection describes the reduction or elimination of the intracellular activity of one or more enzymes (proteins) in a microorganism which are coded by the corresponding DNA, for example by using a weak promoter or using a gene or allele which codes for a corresponding enzyme with a low activity or inactivates the corresponding gene or enzyme (protein), and optionally combining these measures.

The microorganisms to which the present invention relates can prepare amino acids from glucose, sucrose, lactose, fructose, maltose, molasses, starch, cellulose or from glycerol and ethanol. They can be representatives of coryneform bacteria, in particular of the genus Corynebacterium. Of the genus Corynebacterium, there may be mentioned in particular the species *Corynebacterium glutamicum*, which is known among experts for its ability to produce L-amino acids.

Suitable strain of the genus Corynebacterium, in particular of the species *Corynebacterium glutamicum* (*C. glutamicum*), are in particular the known wild-type strains Corynebacterium glutamicum ATCC13032
Corynebacterium acetoglutamicum ATCC15806
Corynebacterium acetoacidophilum ATCC13870
Corynebacterium melassecola ATCC17965
Corynebacterium thermoaminogenes FERM BP-1539
Brevibacterium flavum ATCC14067
Brevibacterium lactofermentum ATCC13869 and
Brevibacterium divaricatum ATCC14020 and L-amino acid-producing mutants or stains prepared thereform.

The new luxS gene from *C. glutamicum* which codes for the histidine kinase LuxS has been isolated. The histidine kinase LuxS is part of a two-component system. Two-component regulation system are distinguished in that various response regulator proteins can be activated by sensor kinases.

To isolate the luxS gene or also other genes of *C. glutamicum*, a gene libaray of this microorganism is first set up in *Escherichia coli* (*E. coli*). The setting up of gene libraries is described in generally known textbooks and handbooks. The textbook by Winnacker: Gene und Klone, Eine Einführung in die Gentechnologie (Verlag Chemie, Weingeim, Germany, 1990), or the handbook by Sambrook et al.: Molecular Cloning, A Laboratory Manual (Cold Spring Harbor Laboratory Press, 1989) may be mentioned as an example. A well-known gene library is that of the *E. coli* K-12 strain W3110 set up in λ vectors by Kohara et al. (Cell 50, 495–508 (1987)). Bathe et al. (Molecular and General Genetics, 252:255–264, 1996) describe a gene library of *C. glutamicum* ATCC13032, which was set up with the aid of the cosmid vector SuperCos I (Wahl et al., 1987, Proceedings of the National Academy of Sciences USA, 84:2160–2164) in the *E. coli* K-12 strain NM554 (Raleigh et al., 1988, Nucleic Acids Research 16:1563–1575).

Börmann et al. (Molecular Microbiology 6(3), 317–326)) (1992)) in turn describe a gene library of *C. glutamicum* ATCC13032 using the cosmid pHC79 (Hohn and Collins, 1980, Gene 11, 291–298).

To prepare a gene library of *C. glutamicum* in *E.coli* it is also possible to use plasmids such as pBR322 (Bolivar, 1979, Life Sciences, 25, 807–818) or pUC9 (Vieira et al., 1982, Gene, 19:259–269). Suitable hosts are, in particular, those *E.coli* strains which are restriction- and recombination-defective, such as, for example, the strain SH5αmcr, which has been described by Grant et al. (Proceedings of the National Academy of Science USA, 87(1990) 4645–4649). The long DNA fragments cloned with the aid of cosmids or other λ vectors can then in tern be subcloned and subsequently sequenced in the usual vectors which are suitable for DNA sequencing, such as is described e.g. be Sanger et al. (Proceedings of the National Academy of Science of the United States of America, 74:5463–5467, 1977).

The resulting DNA sequences can then be investigated with known algorithms or sequences analysis programs, such as e.g. that of Staden (Nucleic Acids Research 14, 217–232(1986)), that of Marck (Nucleic Acids Research 16, 1829–1836 (1988) or the GCG program of Butler (Methods of Biochemical Analysis 39, 74–97 (1998)).

The new DNA sequence of *C. glutamicum* which codes for the luxS gene and which, as SEQ ID No. 1, is a constituent of the present invention has been found. The amino acid sequence of the corresponding protein has furthermore been derived from the present DNA sequence by the methods described above. The resulting amino acid sequence of the luxS gene produce is shown in SEQ ID No. 2.

Coding DNA sequences which result from SEQ ID No. 1 by the degeneracy of the genetic code are also a constituent of the invention. In the same way, DNA sequences which hybridize with SEQ ID No. 1 or parts of SEQ ID No. 1 are a constituent of the invention. Conservative amino acid of aspartic acid for glutamic acid in proteins, are furthermore known among experts as "sense mutations" which do not lead to a fundamental change in the activity of the protein, i.e. are of neutral function. It is furthermore known that changes on the N and/or C terminus of a protein cannot substantially impair or can even stabilize the function thereof. Information in this context can be found by the expert, inter alia, in Ben-Bassat et al. (Journal of Bacteriology 167:751–757 (1987)), in O'Regan et al. (Gene 77:237–251 (1989)), in Sahin-Toth et al. (Protein Sciences 3:240–247 (1994), in Hochuli et al. (Bio/Technology 6:1321–1325 (1988)) and in known textbooks of genetics and molecular biology. Amino acid sequences which result in a corresponding manner from SEQ ID No. 2 are also a constituent of the invention.

In the same way, DNA sequences which hybridize with SEQ ID No. 1 or parts of SEQ ID No. 1 are a constituent of the invention. Finally, DNA sequences which are prepared by the polymerase chain reaction (PCR) using primers which result from SEQ ID No. 1 are a constituent of the invention. Such oligonucleotides typically have a length of al least 15 nucleotides.

Instructions for identifying DNA sequences by means of hybridization can be found by the expert, inter alia, in the handbook "The DIG System Users Guide for Filter Hybridization" from Boehringer Mannheim GmbH (Mannheim, Germany, 1993) and in Liebl et al. (International Journal of Systematic Bacteriology 41: 255–260 (1991)). The hybridization takes place under stringent conditions, that is to say only hybrids in which the probe and target sequence, i.e. the polynucleotides treated with the probe, are at least 70% identical are formed. It is known that the stringency of the hybridization, including the washing steps, is influenced or determined by varying the buffer composition, the temperature and the salt concentration. The hybridization reaction is preferably carried out under a relatively low stringency compared with the washing steps (Hybaid Hybridisation Guide, Hybaid Limited, Teddington, UK, 1996).

A 5×SSC buffer at a temperature of approx. 50–68° C., for example, can be employed for the hybridization reaction. Probes can also hybridize here with polynucleotides which are less than 70% identical to the sequences of the probes. Such hybrids are less stable and are removed by washing under stringent conditions. This can be achieved, for example, by lowering the salt concentration to 2×SSC and optionally subsequently 0.5×SSC (The DIG System User's Guide for Filter Hybridisation, Boehringer Mannheim, Mannheim, Germany, 1995) a temperature of approx. 50–68° C. being established. It is optionally possible to lower the salt concentration to 0.1×SSC. Polynucleotide fragments which are, for example, at least 70% or at least 80% or at least 90% to 95% identical to the sequence of the probe employed can be isolated by increasing the hybridization temperature stepwise from 50 to 68° C. in steps of approx. 1–2° C. Further instructions on hybridization are obtainable on the market in the form of so-called kits (e.g. DIG Easy Hyb from Poche Diagnostics GmbH, Mannheim. Germay, Catalogue No. 1603558).

Instructions for amplification of DNA sequences with the aid of the polymerase chain reaction (PCR) can be found by the expert, inter alia, in the handbook by Gait: Oligonukleotide synthesis: A Practical Approach (IRL Press, Oxford, UK, 1984) and in Newton and Graham: PCR (Spektrum Akademischer Verlag, Heidelberg, Germany, 1994).

It has been found that coryneform bacteria produce amino acids in an improved manner after attenuation of the luxS gene.

To achieve an attenuation, either the expression of the luxS gene or the regulatory or catalytic properties of the enzyme protein can be reduced or eliminated. The two measures can optionally be combined.

The reduction in gene expression can take place by suitable culturing or by; genetic modification (mutation of the signal structures of gene expression. Signal structures of gene expression are, for example, repressor genes, activator genes, operators, promoters, attenuators, ribosome binding sites, the start codon and terminators. The expert can find information on this e.g. in the patent application WO 96/15246, in Boyd and Murphy (Journal of Bacteriology 170: 5949 (1988)), in Voskuil and Chambliss (Nucleic Acids Research 26: 3548 (1998), in Jenson and Hammer (Biotechnology and Bioengineering 58: 191 (1998)), in Pátek et al. (Microbiology 142: 1297 (1996)), Vasicova et al. (Journal of Bacteriology 181: 6188 (1999)) and in known textbooks of genetics and molecular biology, such as e.g. the textbook by Knippers ("Molekulare Genetik", 6th edition, Georg Thieme Verlag, Stuttgart, Germany, 1995) or that by Winnacker ("Gene und Klone", VCH Verlagsgesellschaft, Weinheim, Germany, 1990).

Mutations which lead to a change or reduction in the catalytic properties of enzyme proteins are known from the prior art; examples which may be mentioned are the works by Qiu and Goodman (Journal of Biological Chemistry 272: 8611–8617 (1997)), Sugimoto et al. (Biological Biotechnology and Biochemistry 61: 1760–1762 (1997)) and Möckel ("Die Threonindehydratase aus *Corynebacterium glutamicum*: Aufhenbung der allosterischen Regulation und Struktur des Enzyme", Report from the Jülich Research Centre, Jül-2906, ISSN09442952, Jülich, Germany, 1994). Summarizing descriptions can be found in known textbooks of genetics and molecular biology, such as e.g. that by Hagemann ("Allgemeine Genetik", Gustav Fisher Verlag, Stuttgart, 1986).

Possible mutations are transitions, transversions, insertions and deletions. Depending on the effect of the amino acid exchange on the enzyme activity, "missense mutations" or "nonsense mutations" are referred to. Insertions or deletions of at least one base pair (bp) in a gene lead to frame shift mutations, as a consequence of which incorrect amino acids are incorporated or translation is interrupted prematurely. Deletions of several codons typically lead to a complete loss of the enzyme activity. Instructions on generation of such mutations are prior art and can be found in known textbooks of genetics and molecular biology, such as e.g. the textbook by Knippers ("Molekulare Genetik", 6th edition, Georg Thieme Verlag, Stuttgart, Germany, 1995), that by Winnacker ("Gene und Klone", VCH Verlagsgesellschaft, Weinheim, Germany, 1990) or that by Hagemann ("Allgemeine Genetik", Gustav Fischer Verlag, Stuttgart, 1986).

A common method of mutation genes of *C. glutamicum* is the method of "gene disruption" and "gene replacement" described by Schwarzer and Pühler (Bio/Technology 9, 84–87 (1991)).

In the method of gene disruption a central part of the coding region of the gene of interest is cloned in a plasmid vector which can replicate in a host (typically *E. coli*), but not in *C. glutamicum*. Possible vectors are, for example, pSUP301 (Simon et al., Bio/Technology 1, 784–791 (1983)), pK18mob or pK19mob (Schäfer et al., Gene 145, 69–73 (1994)), pK18mobsacB or pK19mobsacB (Jäger et al., Journal of Bacteriology 174: 5462–65 (1992)), pGEM-T (Promega corporation, Madison, Wis., USA), pCR2.1-TOPO (Shuman (1994). Journal of Biological Chemistry 269:32678–84; U.S. Pat. No. 5,487,993), pCR®Blunt (Invitrogen, Groningen, Holland; Bernard et al., Journal of Molecular Biology, 234: 534–541 (1993)) or pEM1 (Schrumpf et al, 1991, Journal of Bacteriology 173:4510–4516). The plasmid vector which contains the central part of the coding region of the gene is then transferred into the desired strain of *C. glutamicum* by conjugation or transformation. The method of conjugation is described, for example, by Schäfer et al. (Applied and Environmental Microbiology 60, 756–759 (1994)). Methods for transformation are described, for example, by Thierbach et al. (Applied Microbiology and Biotechnology 29, 356–362 (1998)), Dunican and Shivnan (Bio/Technology 7, 1067–1070 (1989)) and Tauch et el. (FEMS Microbiological Letters 123, 343–347 (1994)). After homologous recombination by; means of a "cross-over" event, the coding region of the gene in question is interrupted by the vector sequence and two incomplete alleles are obtained, one lacking the 3' end and one lacking the 5' end. This method has been used, for example, by Fitzpatrick et al. (Applied Microbiology and Biotechnology 42, 575–580 (1994)) to eliminate the recA gene of *C. glutamicum*.

In the method of "gene replacement", a mutation, such as e.g. a deletion, insertion or base exchange, is established in vitro in the gene of interest, The allele prepared is in turn cloned in a vector which is not replicative for *C. glutamicum* and this is then transferred into the desired host of *C. glutamicum* by transformation or conjugation. After homologous recombination by means of a first "cross-over" event which effects intergration and a suitable second "cross-over" event which effects excision in the target gene or in the target sequence, the incorporation of the mutation or of the allele is achieved, This method was used, for example, by Peters-Wendisch et al. (Microbiology 144, 915–927 (1998)) to eliminate the pyc gene of *C. glutamicum* by a deletion.

A deletion, insertion or a base exchange can be incorporated into the luxS gene in this manner.

In addition, it may be advantageous for the production of L-amino acids to enhance, in particular over-express, one or more enzymes of the particular biosynthesis pathway, of glycolysis, of anaplerosis, of the cotric acid cycle, of the pentose phosphate cycle, of amino acid export and optionally regulatory proteins, in addition to the attenuation of the luxS gene.

The term "enhancement" in this connection describes the increase in the intracellular activity of one or more enzymes (proteins) in a microorganism which are coded by the corresponding DNA, for example by increasing the number of copies of the gene or genes, using a potent promoter or using a gene or allele which codes for a corresponding enzyme (protein) having a high activity, and optionally combining these measures.

Thus, for the preparation of L-amino acids, in addition to the attenuation of the luxS gene at the same time one or more of the genes chosen from the group consisting of the dapA gene which codes for dihydrodipicolinate synthase (EP-B 0 197 335), the gap gene which codes for glyceraldehyde 3-phosphate dehydrogenase (Eikmanns (1992), Journal of Bacteriology 174: 6076–6086), the tpi gene which codes for triose phosphate isomerase (Eikmanns (1992), Journal of Bacteriology 174:6076–6086), the pgk gene which codes for 3-phosphoglycerate kinase (Eikmanns (1992), Journal of Bacteriology 174:6076–6086), the zwf gene which codes for glucose 6-phosphate dehydrogenase (JP-A-09224661), the pyc gene which codes for pyruvate carboxylase (DE-A-198 31 609), the mqo gene which codes for malate-quinone oxidoreductase (Molenaar et al., European Journal of Biochemistry 254, 395–403 (1998), the lysC gene which codes for a feed-back resistant aspartate kinase (Accession No. P26512; EP-B-0387527; EP-A-0699759; WO 00/63388), the lysE gene which codes for lysine export (DE-A-195 48 222)

the hom gene which codes for homoserine dehydrogenase (EP-A 0131171), the ilvA gene which codes for threonine dehydratase (Möckel et al., Journal of Bacteriology (1992) 8065–8072)) or the ilvA(Fbr) allele which codes for a "feed back resistant" threonine dehydratase (Möckel et al., (1994) Molecular Microbiology 13: 833–842), the ilvBN gene which codes for acetohydroxy-acid synthase (EP-B 0356739), the ilvD gene which codes for dihydroxy-acid dehydratase (Sahm and Eggeling (1999) Applied and Environmental Microbiology 65: 1973–1979), the zwa1 gene which codes for the Zwa1 protein (DE: 19959328.0, DSM 13115)

can be enhanced, in particular over-expressed.

It may furthermore be advantageous for the production of amino acids, in addition to the attenuation of the luxS gene at the same time for one or more of the genes chosen from the group consisting of the pck gene which codes for phosphoenol pyruvate carboxykinase (DE 199 50 409.1, DSM 13047), the pgi gene which codes for glucose 6-phosphate isomerase(U.S. Ser. No. 09/396,478, DSM 12969), the poxB gene which codes for pyruvate oxidase (DE:1995 1975.7, DSM 13114), the zwa2 gene which codes for the Zwa2 protein (DE: 19959327.2, DSM 13113)

to be attenuated, in particular for the expression thereof to be reduced.

In addition to the attenuation of the luxS gene it may furthermore be advantageous for the production of amino acids to eliminate undesirable side reactions (Nakayama: "Breeding of Amino Acid Producing Microorganisms", in: Overproduction of Microbial Products, Krumphanzl, Sikyta, Vanek (eds.), Academic Press, London, UK, 1982).

The invention also provides the microorganisms prepared according to the invention, and these can be cultured continuously or discontinuously in the batch process (batch culture) or in the fed batch (feed process) or repeated fed batch process (repetitive feed process) for the purpose of production of L-amino acids. A summary of known culture methods is described in the textbook by Chmiel (Bioprozesstechnik 1. Einführung in die Bioverfahrenstechnik (Gustav Fischer Verlag, Stuttgart, 1991)) or in the textbook by Storhas (Bioreaktoren und periphere Einrichtungen (Vieweg Verlag, Braunschweig/Wiesbaden, 1994)).

The culture medium to be used must meet the requirements of the particular strains in a suitable manner. Descriptions of culture media for various microorganisms are contained in the handbook "Manual of Methods for General Bacteriology" of the American Society for Bacteriology (Washington D.C., USA, 1981).

Sugars and carbohydrates, such as e.g. glucose, sucrose, lactose, fructose, maltose, molasses, starch and cellulose, oils and fats, such as, for example, soya oil, sunflower oil, groundnut oil and coconut fat, fatty acids, such as, for example, palmitic acid, stearic acid and linoleic acid, alcohols, such as, for example, glycerol and ethanol, and organic acids, such as, for example, acetic acid, can be used as the source of carbon. These substances can be used individually or as a mixture.

Organic nitrogen-containing compounds, such as peptones, yeast extract, meat extract, malt extract, corn steep liquor, soya bean flour and urea, or inorganic compounds, such as ammonium corbonate and ammonium nitrate, can be phosphate, ammonium carbonate and ammonium chloride, ammonium used as the cource of nitrogen. The sources of nitrogen can be used individually or as a mixture.

Phosphoric acid, potassium dihydrogen phosphate or dipotassium hydrogen phosphate or the corresponding sodium-containing salts can be used as the source of phosphorus. The culture medium must furthermore comprise salts of metals, such as, for example, magnesium sulfate or iron sulfate, which are necessary for growth. Finally, essential growth substances, such as amino acids and vitamins, can be employed in addition to the abovementioned substances. Suitable precursors can moreover be added to the culture medium. The starting substances mentioned can be added to the culture in the form of a single batch, or can be fed in during the culture in a suitable manner.

Basic compounds, such as sodium hydroxide, potassium hydroxide, ammonia or aqueous ammonia, or acid compounds, such as phosphoric acid or sulfuric acid, can be employed in a suitable manner to control the pH of the culture. Antifoams, such as, for example, fatty acid polyglycol esters, can be employed to control the development of foam. Suitable substances having a selective action, such as, for example, antibiotics, can be added to the medium to maintain the stability of plasmids. To maintain aerobic conditions, oxygen or oxygen-containing gas mixtures, such as, for example, air, are introduced into the culture. The temperature of the culture is usually 20° C. to 45° C., and preferably 25° C. to 40° C. Culturing is continued until a maximum of the desired product has formed. This target is usually reached within 10 hours to 160 hours.

Methods for the determination of L-amino acids are known from the prior art. The analysis can thus be carried out, for example, as described by Spackman et al. (Analytical Chemistry, 30, (1958), 1190) by anion exchange chromatography with subsequent ninhydrin derivatization, or it can be carried out by reversed phase HPLC, for example as described by Lindroth et al. (Analytical Chemistry (1979) 51: 1167–1174).

The process according to the invention is used for fermentative preparation of amino acids.

The following microorganism was deposited as a pure culture on Feb. 26, 2001 at the Deutsche Sammlung fur Mikroorganismen und Zellkulturen (DSMZ=German Collection of Microorganisms and Cell Cultures, Mascheroder Weg 1b, D-38124, Braunschweig, Germany) in accordance with the Budapest Treaty.

*Escherichia coli* Top10/pCR2.1luxSint as DSM 14082.

The present invention is explained in more detail in the following with the aid of embodiment examples.

The isolation of plasmid DNA from *Escherichia coli* and all techniques of restriction, Klenow and alkaline phosphatase treatment were carried out by the method of Sambrook et al. (Molecular Cloning. A Laboratory Manual, 1989, Cold Spring Harbour Laboratory Press, Cold Spring Harbor, N.Y., USA). Methods for transformation of *Escherichia coli* are also described in this handbook.

The composition of the usual nutrient media, such as LB or TY medium, can also be found in the handbook by Sambrook et al.

EXAMPLE 1

Preparation of a Genomic Cosmid Gene Library from *C. glutamicum* ATCC 13032

Chromosomal DNA from *C. glutamicum* ATCC 13032 was isolated as described by Tauch et al. (1995, Plasmid 33:168–179) and partly cleaved with the restriction enzyme Sau3AI (Amersham Pharmacia, Freiburg, Germany, Product Description Sau3AI, Code no. 27-0913-02). The DNA fragments were dephosphorylated with shrimp alkaline phosphatase (Roche Molecular Biochemicals, Mannheim, Germany, Product Description SAP, Code no. 1758250). The DNA of the cosmid vector SuperCosl (Wahl et al. (1987), Proceedings of the National Academy of Sciences, USA 84:2160–2164), obtained from Stratagene (La Jolla, USA, Product Description SuperCos1 Cosmid Vector Kit, Code no. 251301) was cleaved with the restriction enzyme XbaI (Amersham Pharmacia, Freiburg, Germany, Product Description XbaI, Code no. 27-0948-02) and likewise dephosphorylated with shrimp alkaline phosphatase.

The cosmid DNA was then cleaved with the restriction enzyme BamHI (Amersham Pharmacia, Freiburg, Germany, Product Description BamHI, Code no. 27-0868-04). The cosmid DNA treated in this manner was mixed with the treated ATCC13032 DNA and the batch was treated with T4 DNA ligase (Amersham Pharmacia, Freiburg, Germany, Product Description T4-DNA-Ligase, Code no.27-0870-04). The ligation mixture was then packed in phages with the aid of Gigapack II XL Packing Extract (Stratagene, La Jolla, USA, Product Description Gigapack II XL Packing Extract, Code no. 200217).

For infection of the *E. coli* strain NM554 (Raleigh et al. 1988, Nucleic Acid Res. 16:1563–1575) the cells were taken up in 10 mM $MgSO_4$ and mixed with an aliquot of the phage suspension. The infection and titering of the cosmid library were carried out as described by Sambrook et al. (1989, Molecular Cloning: A Laboratory Manual, Cold Spring Harbor), the cells being plated out on LB agar (Lennox, 1955, Virology, 1:190)+100 µg/ml ampicillin. After incubation overnight at 37° C., recombinant individual clones were selected.

EXAMPLE 2

Isolation and Sequencing of the luxS Gene

The cosmid DNA of an individual colony was isolated with the Qiaprep Spin Miniprep Kit (Product No. 27106, Qiagen, Hilden, Germany) in accordance with the manufacturer's instructions and partly cleaved with the restriction enzyme Sau3AI (Amersham Pharmacia, Freiburg, Germany, Product Description Sau3AI, Product No. 27-0913-02). The DNA fragments were dephosphorylated with shrimp alkaline phosphatase (Roche Molecular Biochemicals, Mannheim, Germany, Product Description SAP, Product No. 1758250). After separation by gel electrophoresis, the cosmid fragments in the size range of 1500 to 2000 bp were isolated with the QiaExII Gel Extraction Kit (Product No. 20021, Qiagen, Hilden, Germany).

The DNA of the sequencing vector pZero-1, obtained from Invitrogen (Groningen, The Netherlands, Product Description Zero Background Cloning Kit, Product No. K2500-01) was cleaved with the restriction enzyme BamHI (Amersham Pharmacia, Freiburg, Germany, Product Description BamHI, Product No. 27-0868-04). The ligation of the cosmid fragments in the sequencing vector pZero-1 was carried out as described by Sambrook et al. (1989, Molecular Cloning: A Laboratory Manual, Cold Spring Harbor), the DNA mixture being incubated overnight with T4 ligase (Pharmacia Biotech, Freiburg, Germany). This ligation mixture was then electroporated (Tauch et al. 1994, FEMS Microbiol. Letters, 123:343–7) into the *E. coli* strain DH5α mcr (Grant, 1990, Proceedings of the National Academy of Sciences, U.S.A., 87:4645–4649). Letters, 123:343–7) and plated out on LB agar (Lennox, 1955, Virology, 1:190) with 50 mg/l zeocin.

The plasmid preparation of the recombinant clones was carried out with Biorobot 9600 (Product No. 900200, Qiagen, Hilden, Germany). The sequencing was carried out by the dideoxy chain termination method of Sanger et al. (1977, Proceedings of the National Academies of Sciences, U.S.A., 74:5463–5467) with modifications according to Zimmermann et al. (1990, Nucleic Acids Research, 18:1067). The "RR dRhodamin Terminator Cycle Sequencing Kit" from PE Applied Biosystems (Product No. 403044, Weiterstadt, Germany) was used. The separation by gel electrophoresis and analysis of the sequencing reaction were carried out in a "Rotiphoresis NF Acrylamide/ Bisacrylamide" Gel (29:1) (Product No. A124.1, Roth, Karlsruhe, Germany) with the "ABI Prism 377" sequencer from PE Applied Biosystems (Weiterstadt, Germany).

The raw sequence data obtained were then processed using the Staden program package (1986, Nucleic Acids Research, 14:217–231) version 97-0. The individual sequences of the pZero1 derivatives were assembled to a continuous contig. The computer-assisted coding region analysis were prepared with the XNIP program (Staden, 1986, Nucleic Acids Research, 14:217–231). Further analyses were carried out with the "BLAST search program" (Altschul et al., 1997, Nucleic Acids Research, 25:3389–3402) against the non-redundant databank of the "National Center for Biotechnology Information" (NCBI, Bethesda, Md, USA).

The resulting nucleotide sequence is shown in SEQ ID No. 1. Analysis of the nucleotide sequence showed an open reading frame of 1272 bp, which was called the luxS gene. The luxS gene codes for a polypeptide of 423 amino acids.

EXAMPLE 3

Preparation of an Integration Vector for Integration Mutagenesis of the luxS Gene From the strain ATCC 13032, chromosomal DNA was isolated by the method of Eikmanns et al. (Microbiology 140: 1817–1828 (1994)). On the basis of the sequence of the luxS gene known for *C. glutamicum* from example 2, the following oligonucleotides were chosen for the polymerase chain reaction (see SEQ ID No. 3 and SEQ ID No. 4):

```
luxS-int1:
5' TCG TGA CCG TGG CTA TTG AT 3' luxS-int2:
5' CTT GAG CAA TTC GCA GAA GG 3'
```

The primers shown were synthesized by MWG Biotech (Ebersberg, Germany) and the PCR reaction was carried out by the standard PCR method of Innis et al. (PCR protocols. A guide to methods and applications, 1990, Academic Press) with the Taq-polymerase from Boehringer Mannheim (Germany, Product Description Taq DNA polymerase, Product No. 1 146 165). With the aid of the polymerase chain reaction, the primers allow amplification of an internal fragment of the luxS gene 492 bp in size. The product amplified in this way was tested electrophoretically in a 0.8% agarose gel.

The amplified DNA fragment was ligated with the TOPO TA Cloning Kit from Invitrogen Corporation (Carlsbad, Calif., USA; Catalogue Number K4500-01) in the vector pCR2.1-TOPO (Mead at al. (1991) Bio/Technology 9:657–663).

The *E. coli* strain TOP10 was then electroporated with the ligation batch (Hanahan, In: DNA cloning. A practical approach. Vol.I. IRL-Press, Oxford, Washington D.C., USA, 1985). Selection of plasmid-carrying cells was carried out by plating out the transformation batch on LB Agar (Sambrook et al., Molecular cloning: a laboratory manual. $2^{nd}$ Ed. Cold Spring Harbor Laboratory Press, Cold Spring Harbor, N.Y., 1989), which had been supplemented with 50 mg/l kanamycin. Plasmid DNA was isolated from a transformant with the aid of the QIAprep Spin Miniprep Kit from Qiagen and checked by restriction with the restriction enzyme EcoRI and subsequent agarose gel electrophoresis (0.8%). The plasmid was called pCR2.1luxSint and is shown in FIG. 1.

EXAMPLE 4

Integration Mutagenesis of the luxS Gene in the Strain DSM 5715

The vector pCR2.1luxSint mentioned in example 3 was electroporated by the electroporation method of Tauch et al. (FEMS Microbiological Letters, 123:343–347 (1994)) in *Corynebacterium glutamicum* DSM 5715. The strain DSM 5715 is an AEC-resistant lysine producer. The vector pCR2.1luxSint cannot replicate independently in DSM5715 and is retained in the cell only if it has integrated into the chromosome of DSM 5715. Selection of clones with pCR2.1luxSint integrated into the chromosome was carried out by plating out the electroporation batch on LB agar (Sambrook et al., Molecular cloning: a laboratory manual. $2^{nd}$ Ed. Cold Spring Harbor Laboratory Press, Cold Spring Harbor, N.Y.), which had been supplemented with 15 mg/l kanamycin.

For detection of the integration, the luxSint fragment was labelled with the Dig hybridization kit from Boehringer by the method of "The DIG System Users Guide for Filter Hybridization" of Boehringer Mannheim GmbH (Mannheim, Germany, 1993). Chromosomal DNA of a potential integrant was isolated by the method of Eikmanns et al. (Microbiology 140: 1817–1828 (1994)) and in each case cleaved with the restriction enzymes SalI, EcoRI and PstI. The fragments formed were separated by means of agarose gel electrophoresis and hybridized at 68° C. with the Dig hybrization kit from Boehringer. The plasmid pCR2.1luxSint mentioned in example 3 had been inserted into the chromosome of DSM5715 within the chromosomal luxS gene. The strain was called DSM5715::pCR2.1luxSint.

EXAMPLE 5

Preparation of Lysine

The *C. glutamicum* strain DSM5715::pCR2.1luxSint obtained in example 4 was cultured in a nutrient medium suitable for the production of lysine and the lysine content in the culture supernatant was determined.

For this, the strain was first incubated on an agar plate with the corresponding antibiotic (brain-heart agar with kanamycin (25 mg/l) for 24 hours at 33° C. Starting from this agar plate culture, a preculture was seeded (10 ml medium in a 100 ml conical flask). The complete medium CgIII was used as the medium for the preculture.

| Medium Cg III | |
|---|---|
| NaCl | 2.5 g/l |
| Bacto-Peptone | 10 g/l |
| Bacto-Yeast extract | 10 g/l |
| Glucose (autoclaved separately) | 2% (w/v) |
| The pH was brought to pH 7.4 | |

Kanamycin (25 mg/l) was added to this. The preculture was incubated for 16 hours at 33° C. at 240 rpm on a shaking machine. A main culture was seeded from this preculture such that the initial OD (660 nm) of the main culture was 0.1 OD. Medium MM was used for the main culture.

| Medium MM | |
|---|---|
| CSL (corn steep liquor) | 5 g/l |
| MOPS (morpholinopropanesulfonic acid) | 20 g/l |
| Glucose (autoclaved separately) | 50 g/l |
| Salts: | |
| $(NH_4)_2SO_4)$ | 25 g/l |
| $KH_2PO_4$ | 0.1 g/l |
| $MgSO_4 * 7 H_2O$ | 1.0 g/l |
| $CaCl_2 * 2 H_2O$ | 10 mg/l |
| $FeSO_4 * 7 H_2O$ | 10 mg/l |
| $MnSO_4 * H_2O$ | 5.0 mg/l |
| Biotin (sterile-filtered) | 0.3 mg/l |
| Thiamine * HCl (sterile-filtered) | 0.2 mg/l |

-continued

| Medium MM | |
|---|---|
| Leucine (sterile-filtered) | 0.1 g/l |
| CaCO$_3$ | 25 g/l |

The CSL, MOPS and the salt solution are brought to pH 7 with aqueous ammonia and autoclaved. The sterile substrate and vitamin solutions are then added, and the CaCO$_3$ autoclaved in the dry state is added.

Culturing is carried out in a 10 ml volume in a 100 ml conical flask with baffles. Kanamycin (25 mg/l) was added. Culturing was carried out at 33° C. and 80% atmospheric humidity.

After 72 hours, the OD was determined at a measurement wavelength of 660 nm with a Biomek 1000 (Beckmann Instruments GmbH, Munich). The amount of lysine formed was determined with an amino acid analyzer from Eppendorf-BioTronik (Hamburg, Germany) by ion exchange chromatography and post-column derivatization with ninhydrin detection.

The result of the experiment is shown in table 1.

TABLE 1

| Strain | OD (660 nm) | Lysine HCl g/l |
|---|---|---|
| DSM5715 | 8.0 | 12.64 |
| DSM5715::pCR2.11uxSint | 9.3 | 14.39 |

DESCRIPTION OF THE FIGURE

FIG. 1: Map of the plasmid pCR2.1luxSint.

The abbreviations and designations used have the following meaning.

| KmR: | Kanamycin resistance gene |
|---|---|
| EcoRI: | Cleavage site of the restriction enzyme EcoRI |
| PstI: | Cleavage site of the restriction enzyme PstI |
| SalI: | Cleavage site of the restriction enzyme SalI |
| luxSint: | Internal fragment of the luxS gene |
| ColE1: | Replication origin of the plasmid ColE1 |

What is claimed is:

1. An isolated polynucleotide comprising SEQ ID NO:1.
2. An isolated polynucleotide comprising the full complement of SEQ ID NO:1.
3. A vector comprising the isolated polynucleotide of Claim 1.
4. A bacterium comprising the vector of claim 3.
5. The bacterium of claim 4, wherein said bacterium is of the species *Escherichia coil* or of the genus Corynebacterium.
6. The vector pCR2.1luxSint contained in the *E. coli* strain Top10/pCR2.1luxSint (DSM Accession No. 14082).
7. A method for the fermentative preparation of L-lysine, the method comprising:
  a) fermentation of an L-lysine producing *Corynebacterium glutamicum* bacteria into which the vector of claim 6 has been transformed,
  b) concentration of L-lysine in the medium or in the cells of the bacteria, and
  c) isolation of L-lysine.

* * * * *

UNITED STATES PATENT AND TRADEMARK OFFICE
CERTIFICATE OF CORRECTION

PATENT NO.    : 6,746,854 B2
DATED         : June 8, 2004
INVENTOR(S)   : Brigitte Bathe et al.

It is certified that error appears in the above-identified patent and that said Letters Patent is hereby corrected as shown below:

Title page,
Item [22], PCT Filed, replace "Aug. 1, 2001" with -- April 4, 2001 --.

Signed and Sealed this

Seventh Day of February, 2006

JON W. DUDAS
*Director of the United States Patent and Trademark Office*

```
                       SEQUENCE LISTING

<160> NUMBER OF SEQ ID NOS: 4

<210> SEQ ID NO 1
<211> LENGTH: 1902
<212> TYPE: DNA
<213> ORGANISM: Corynebacterium glutamicum
<220> FEATURE:
<221> NAME/KEY: CDS
<222> LOCATION: (342)..(1610)
<223> OTHER INFORMATION: luxS-Gen

<400> SEQUENCE: 1
ggtaggagta aaaaacgcag gagggcgtcg aaaagcgttc gtctgtgccg taacccgtga        60
cgcgctggcc gttggtatcg gcgacccagt cggtgcccag gtagggcat gcggtttgtg       120 cggtgcgttc daccgcgggc atcgcgtcga tgggaaggcc gtcagtaatt acttccgggg      180
ctgcctcggt ggtggtctct gggggttgctt caggttccgc cggggtacaa gcggtgagca    240
tgatggaagc agcgaggata gtaggtaatg tacgacgcat gcagtcaagc ctagatcgtg    300
tgtcggaaac cggacgcaat gagctcgatg ttgaaaccct t gtg aag aag ggg aat    356
                                           Met Lys Lys Gly Asn
                                             1               5 caa ccg ggc gcg atg agc tat cgc aac agt atc cac att ttg aca gcc        404
Gln Pro Gly Ala Met Ser Tyr Arg Asn Ser Ile His Ile Leu Thr Ala
           10                  15                  20 tcg ctg ctg gtc gtg ggg ttg gga gct tcc gcc cgc ctg acg ctg ccg        452
Ser Leu Leu Val Val Gly Leu Gly Ala Ser Ala Arg Leu Thr Leu Pro
       25                  30                  35 atg ttt gcg ctg tcg tgc gtg ctg ttg ttt gtg tgg ggt ttt ctg tac       500
Met Phe Ala Leu Ser Cys Val Leu Leu Phe Val Trp Gly Phe Leu Tyr
   40                  45                  50 ttc tat gga tca acc aaa cgc gta gat ttg agc cac ggc atg cag ctg       548
Phe Tyr Gly Ser Thr Lys Arg Val Asp Leu Ser His Gly Met Gln Leu
 55                  60                  65 ggc tgg ctg ttt gtg ctg acg ctg gtg tgg att ttt atg gtg ccg atc       596
Gly Trp Leu Phe Val Leu Thr Leu Val Trp Ile Phe Met Val Pro Ile
 70                  75                  80                  85
```

-continued

| | |
|---|---|
| gtg ccc gtg tcc att tat ctg ctg ttc ccg ctg ttt ttc ctc tat cta<br>Val Pro Val Ser Ile Tyr Leu Leu Phe Pro Leu Phe Phe Leu Tyr Leu<br>                              90                         95                    100 | 644 |
| cag gtg atg cct gac gtg aga ggc att att gcg att ttg ggt gcg aca<br>Gln Val Met Pro Asp Val Arg Gly Ile Ile Ala Ile Leu Gly Ala Thr<br>                  105                    110                    115 | 692 |
| gcg att gcg att gcc agc cag tat tcc gtg ggg ttg acc ttt ggt ggt<br>Ala Ile Ala Ile Ala Ser Gln Tyr Ser Val Gly Leu Thr Phe Gly Gly<br>        120                    125                    130 | 740 |
| gtg atg ggt ccg gtg gtc tct gcg atc gtg acc gtg gct att gat tac<br>Val Met Gly Pro Val Val Ser Ala Ile Val Thr Val Ala Ile Asp Tyr<br>135                    140                    145 | 788 |
| gcg ttc cgc acg ttg tgg cgg gtg aat aat gaa aag cag gaa ttg att<br>Ala Phe Arg Thr Leu Trp Arg Val Asn Asn Glu Lys Gln Glu Leu Ile<br>150                    155                    160                    165 | 836 |
| gat cag ttg att gaa act cgc tcc cag ctg gcg gtg acg gaa cga aat<br>Asp Gln Leu Ile Glu Thr Arg Ser Gln Leu Ala Val Thr Glu Arg Asn<br>                  170                    175                    180 | 884 |
| gcg ggt att gct gcg gaa cgt caa cgt att gcg cat gaa att cat gac<br>Ala Gly Ile Ala Ala Glu Arg Gln Arg Ile Ala His Glu Ile His Asp<br>        185                    190                    195 | 932 |
| acg gtc gcc cag gga ctc tcc tcc att caa atg ctg ctg cat gtc tct<br>Thr Val Ala Gln Gly Leu Ser Ser Ile Gln Met Leu Leu His Val Ser<br>200                    205                    210 | 980 |
| gaa cag gag att ctc gtt gct gag atg gaa gag aag cca aag gag gcg<br>Glu Gln Glu Ile Leu Val Ala Glu Met Glu Glu Lys Pro Lys Glu Ala<br>        215                    220                    225 | 1028 |
| atc gtg aag aag atg cgc ctt gcc cga caa aca gcc tcc gac aat ctc<br>Ile Val Lys Lys Met Arg Leu Ala Arg Gln Thr Ala Ser Asp Asn Leu<br>230                    235                    240                    245 | 1076 |
| agt gag gct cgc gcg atg att gcg gcg ttg caa ccg gca gcg ctg tct<br>Ser Glu Ala Arg Ala Met Ile Ala Ala Leu Gln Pro Ala Ala Leu Ser<br>                  250                    255                    260 | 1124 |
| aaa acc tcc ttg gaa gca gca ctt cac cgc gtc aca gaa ccg ttg ttg<br>Lys Thr Ser Leu Glu Ala Ala Leu His Arg Val Thr Glu Pro Leu Leu<br>        265                    270                    275 | 1172 |
| ggt att aat ttt gtg att tct gtc gac ggt gat gtt cgc caa ctg ccc<br>Gly Ile Asn Phe Val Ile Ser Val Asp Gly Asp Val Arg Gln Leu Pro<br>280                    285                    290 | 1220 |
| atg aaa act gaa gcc acc ctt ctg cga att gct caa ggt gcg atc gga<br>Met Lys Thr Glu Ala Thr Leu Leu Arg Ile Ala Gln Gly Ala Ile Gly<br>        295                    300                    305 | 1268 |
| aat gtg gcg aaa cat tca gag gcg aaa aac tgc cac gtg aca cta acc<br>Asn Val Ala Lys His Ser Glu Ala Lys Asn Cys His Val Thr Leu Thr<br>310                    315                    320                    325 | 1316 |
| tac gaa gac aca gaa gta cgc ctt gat gtg gtt gat gac ggt gtg ggt<br>Tyr Glu Asp Thr Glu Val Arg Leu Asp Val Val Asp Asp Gly Val Gly<br>                  330                    335                    340 | 1364 |
| ttt gag cct tcg gaa gtg tcc agt acc ccc gct ggc ttg ggc cat atc<br>Phe Glu Pro Ser Glu Val Ser Ser Thr Pro Ala Gly Leu Gly His Ile<br>                  345                    350                    355 | 1412 |
| ggc tta acc gca ttg cag cag cgt gcg atg gaa ttg cac ggc gaa gtt<br>Gly Leu Thr Ala Leu Gln Gln Arg Ala Met Glu Leu His Gly Glu Val<br>                  360                    365                    370 | 1460 |
| ata gtg gaa tct gca tat ggg cag ggt act gcg gta tct gca gca ttg<br>Ile Val Glu Ser Ala Tyr Gly Gln Gly Thr Ala Val Ser Ala Ala Leu<br>375                    380                    385 | 1508 |
| ccg gtg gag cca cca gag ggg ttt gtc ggg gcg ccg gtt ttg gca gat<br>Pro Val Glu Pro Pro Glu Gly Phe Val Gly Ala Pro Val Leu Ala Asp | 1556 |

-continued

```
                390                 395                 400                 405 tcg gac tca agt gct aca ggc gag gtt gaa cta agt tct cca act gac         1604
Ser Asp Ser Ser Ala Thr Gly Glu Val Glu Leu Ser Ser Pro Thr Asp
                410                 415                 420 gat gag taaggctaga ctaaagtacg attcatctgc tcatcgatac tcttgaaggc          1660
Asp Glu gcattttcat tcgaaacgaa gtgcgccatt gggaaggacc tagttcaaac aatgattcgc       1720
gtgctgcttg ctgatgacca cgaaatcgtg aggctcggac tccgagctgt gctggaaagc       1780
gccgaggaca ttgaagtggt gggcgaagtc tccaccgccg aaggtgcggt gcaggcagcc       1840
caagaaggcg aatcgacgt catcttgatg gacctccgat tcggccccgg cgtccaagga        1900
ac                                                                      1902
```

<210> SEQ ID NO 2
<211> LENGTH: 423
<212> TYPE: PRT
<213> ORGANISM: Corynebacterium glutamicum

<400> SEQUENCE: 2

```
Met Lys Lys Gly Asn Gln Pro Gly Ala Met Ser Tyr Arg Asn Ser Ile
  1               5                  10                  15

His Ile Leu Thr Ala Ser Leu Leu Val Val Gly Leu Gly Ala Ser Ala
             20                  25                  30

Arg Leu Thr Leu Pro Met Phe Ala Leu Ser Cys Val Leu Leu Phe Val
         35                  40                  45

Trp Gly Phe Leu Tyr Phe Tyr Gly Ser Thr Lys Arg Val Asp Leu Ser
     50                  55                  60

His Gly Met Gln Leu Gly Trp Leu Phe Val Leu Thr Leu Val Trp Ile
 65                  70                  75                  80

Phe Met Val Pro Ile Val Pro Val Ser Ile Tyr Leu Leu Phe Pro Leu
                 85                  90                  95

Phe Phe Leu Tyr Leu Gln Val Met Pro Asp Val Arg Gly Ile Ile Ala
            100                 105                 110

Ile Leu Gly Ala Thr Ala Ile Ala Ile Ala Ser Gln Tyr Ser Val Gly
        115                 120                 125

Leu Thr Phe Gly Gly Val Met Gly Pro Val Val Ser Ala Ile Val Thr
    130                 135                 140

Val Ala Ile Asp Tyr Ala Phe Arg Thr Leu Trp Arg Val Asn Asn Glu
145                 150                 155                 160

Lys Gln Glu Leu Ile Asp Gln Leu Ile Glu Thr Arg Ser Gln Leu Ala
                165                 170                 175

Val Thr Glu Arg Asn Ala Gly Ile Ala Ala Glu Arg Gln Arg Ile Ala
            180                 185                 190

His Glu Ile His Asp Thr Val Ala Gln Gly Leu Ser Ser Ile Gln Met
        195                 200                 205

Leu Leu His Val Ser Glu Gln Glu Ile Leu Val Ala Glu Met Glu Glu
    210                 215                 220

Lys Pro Lys Glu Ala Ile Val Lys Lys Met Arg Leu Ala Arg Gln Thr
225                 230                 235                 240

Ala Ser Asp Asn Leu Ser Glu Ala Arg Ala Met Ile Ala Ala Leu Gln
                245                 250                 255

Pro Ala Ala Leu Ser Lys Thr Ser Leu Glu Ala Ala Leu His Arg Val
            260                 265                 270

Thr Glu Pro Leu Leu Gly Ile Asn Phe Val Ile Ser Val Asp Gly Asp
```

-continued

```
                275              280              285
Val Arg Gln Leu Pro Met Lys Thr Glu Ala Thr Leu Leu Arg Ile Ala
    290             295             300

Gln Gly Ala Ile Gly Asn Val Ala Lys His Ser Glu Ala Lys Asn Cys
305             310             315             320

His Val Thr Leu Thr Tyr Glu Asp Thr Glu Val Arg Leu Asp Val Val
            325             330             335

Asp Asp Gly Val Gly Phe Glu Pro Ser Glu Val Ser Ser Thr Pro Ala
            340             345             350

Gly Leu Gly His Ile Gly Leu Thr Ala Leu Gln Gln Arg Ala Met Glu
            355             360             365

Leu His Gly Glu Val Ile Val Glu Ser Ala Tyr Gly Gln Gly Thr Ala
    370             375             380

Val Ser Ala Ala Leu Pro Val Glu Pro Pro Glu Gly Phe Val Gly Ala
385             390             395             400

Pro Val Leu Ala Asp Ser Asp Ser Ser Ala Thr Gly Glu Val Glu Leu
            405             410             415

Ser Ser Pro Thr Asp Asp Glu
            420
```

<210> SEQ ID NO 3
<211> LENGTH: 20
<212> TYPE: DNA
<213> ORGANISM: Corynebacterium glutamicum
<220> FEATURE:
<223> OTHER INFORMATION: Primer luxS-int1

<400> SEQUENCE: 3
tcgtgaccgt ggctattgat                                          20

<210> SEQ ID NO 4
<211> LENGTH: 20
<212> TYPE: DNA
<213> ORGANISM: Corynebacterium glutamicum
<220> FEATURE:
<223> OTHER INFORMATION: Primer luxS-int2

<400> SEQUENCE: 4
cttgagcaat tcgcagaagg                                          20